US008457595B2

(12) United States Patent
MacInnis et al.

(10) Patent No.: US 8,457,595 B2
(45) Date of Patent: Jun. 4, 2013

(54) METHOD AND SYSTEM FOR PROCESSING INFORMATION BASED ON DETECTED BIOMETRIC EVENT DATA

(75) Inventors: Alexander MacInnis, Ann Arbor, MI (US); Arya Behzad, Poway, CA (US); Mark Buer, Gilbert, AZ (US); Jeyhan Karaoguz, Irvine, CA (US); Thomas Quigley, Franklin, NC (US); John Walley, Ladera Ranch, CA (US)

(73) Assignee: Broadcom Corporation, Irvine, CA (US)

( * ) Notice: Subject to any disclaimer, the term of this patent is extended or adjusted under 35 U.S.C. 154(b) by 897 days.

(21) Appl. No.: 11/861,786

(22) Filed: Sep. 26, 2007

(65) Prior Publication Data
US 2009/0023422 A1 Jan. 22, 2009

Related U.S. Application Data

(60) Provisional application No. 60/950,952, filed on Jul. 20, 2007.

(51) Int. Cl.
*H04M 1/66* (2006.01)
(52) U.S. Cl.
USPC .......... 455/410; 455/41.2; 382/115; 382/116; 382/124
(58) Field of Classification Search
USPC ......... 455/410, 41.2; 382/115–124; 340/5.83, 340/10.1, 573.1
See application file for complete search history.

(56) References Cited

U.S. PATENT DOCUMENTS

| 5,552,806 | A | 9/1996 | Lenchik |
| 5,646,608 | A | 7/1997 | Shintani |
| 6,314,297 | B1 | 11/2001 | Karl |
| 7,203,486 | B2 | 4/2007 | Patel |
| 2003/0163710 | A1* | 8/2003 | Ortiz et al. ................ 713/186 |
| 2007/0239991 | A1 | 10/2007 | Cheng |
| 2008/0002861 | A1* | 1/2008 | Yano et al. ................ 382/115 |
| 2009/0002178 | A1* | 1/2009 | Guday et al. .............. 340/573.1 |
| 2009/0207252 | A1* | 8/2009 | Raghunath ................ 348/158 |

FOREIGN PATENT DOCUMENTS

| EP | 1045355 A1 | 10/2000 |
| WO | 2005078676 A2 | 8/2005 |

OTHER PUBLICATIONS

Seagate Technology LLC, Seagate D.A.V.E. (Digital Audio Video Experience) Transform the consumer digital content experience with the Seagate D.A.V.E design concept, Data Sheet, 2007.

(Continued)

*Primary Examiner* — Patrick Edouard
*Assistant Examiner* — Julio Perez
(74) *Attorney, Agent, or Firm* — Thomas Horstemeyer, LLP

(57) ABSTRACT

A system and method is provided for processing and storing captured data in a wireless communication device based on detected biometric event data. The captured data may be acquired through a data acquisition system with devices or sensors in an integrated or distributed configuration. The captured data may include multimedia data of an event with time, date and/or location stamping, and captured physiological and behavioral biometric event data in response to the event. The captured data may be dynamically stored in a data binding format or as raw data in a local host device or communicated externally to be stored in a remote host or storage. At least one user preference may be specified for linking a biometric event data to the mapped, analyzed, categorized and stored captured data in a database. Captured data may be retrieved by matching biometric event data to at least one user preference from the database.

28 Claims, 6 Drawing Sheets

OTHER PUBLICATIONS

Seagate Technology LLC, Seagate D.A.V.E. (Digital Audio Video Experience) The portable storage platform that collects, plays and manages digital content, Product Overview, 2007.

TODAYSTHV.COM, KTHV Little Rock (Mind-Reading Toys Wave of the Future) The Associated Press, Apr. 30, 2007.

International Search Report, PCT/IL 2005/000191, mailed Sep. 9, 2005, 5 pages.

* cited by examiner

Biometric Data
Mapping Table 134

| | E+ | E- | M+ | M- | C+ | C- | P+ | P- | ... |
|---|---|---|---|---|---|---|---|---|---|
| | Mood Condition 134b | | Mental State 134c | | Character Condition 134d | | Physical Condition 134a | | |
| 1 | Happy | Upset | Decisive | Hesitant | Truthful | Not Truthful | | Hungry | |
| 2 | Peaceful | Agitated | Confident | Lack Confidence | Credible | Not Credible | Comfortable | Cold | |
| 3 | Pleased | Angry | Calm | Startled | Kind | Unkind | | Hot | → BD4, BD8 |
| 4 | Excited | Outraged | Alert | Unclear | Aggressive | Passive | | Fever | |
| 5 | Relaxed | Rushed | Agreement | Disagreement | Courteous | Uncourteous | Relaxed | Blood Pressure Rise | → BD7 |
| 6 | | Anxious | | | Enthusiastic | Indifferent | | Nausea | |
| 7 | Uplifting | Sad | ... | | Proactive | Reactive | | Sweating | → BD8 |
| 8 | | Grief | | | Brave | Timid | | Breathing Rate Rise | → BD5 |
| 9 | Hopeful | Depressed | | | Pleasant | Rude | Muscle Relax | Muscle Tension | → BD6 |
| 10 | Motivated | Demotivated | | | Deliberate | Unfocused | Comfortable | Uncomfortable | |
| 11 | Satisfied | Dissatisfied | | | ... | ... | Strong | Weak | BD1, BD4, BD5, BD6, BD75 |
| 12 | ... | ... | | | | | Loud | Soft | |
| 13 | | | | | | | ... | ... | |

METHOD AND SYSTEM FOR PROCESSING INFORMATION BASED ON DETECTED BIOMETRIC EVENT DATA

CROSS-REFERENCE TO RELATED APPLICATIONS/INCORPORATION BY REFERENCE

This application makes reference to, claims priority to, and claims the benefit of U.S. Provisional Application Ser. No. 60/950,952 filed on Jul. 20, 2007.

This application also makes reference to:
U.S. patent application Ser. No. 11/861,224 filed on Sep. 25, 2007;
U.S. patent application Ser. No. 11/861,220 filed on Sep. 25, 2007; and
U.S. patent application Ser. No. 11/861,219 filed on Sep. 25, 2007.

Each of the above stated applications is hereby incorporated herein by reference in its entirety

FIELD OF THE INVENTION

Certain embodiments of the invention relate to wireless communication. More specifically, certain embodiments of the invention relate to a method and system for processing information based on detected biometric event data.

BACKGROUND OF THE INVENTION

The field of wireless communication has seen dramatic growth over the last few years. Currently, most people use their wireless devices, be it cellular phones, PDA's, laptops, and/or other devices, for various purposes, business and personal, on a constant and daily basis. Society is truly becoming a wireless one. Many wireless solutions have been introduced, and have made tremendous strides into everyday life.

For example, the use of Wireless Personal Area Networks (WPAN) has been gaining popularity in a great number of applications because of the flexibility and convenience in connectivity they provide. WPAN systems generally replace cumbersome cabling and/or wiring used to connect peripheral devices and/or mobile terminals by providing short distance wireless links that allow connectivity within very narrow spatial limits. WPAN may be based on standardized technologies, for example Class 2 Bluetooth© technology. While WPAN may be very beneficial for certain applications, other applications may require larger service areas and/or capabilities.

To satisfy such needs, other technologies have been developed to provide greater wireless service. Wireless Local Area Networks (WLAN) systems may operate within a wider range. In contrast to the WPAN systems, WLAN provide connectivity to devices that are located within a slightly larger geographical area, such as the area covered by a building or a campus. WLAN systems are generally based on specific standards, for example IEEE 802.11 standard specifications to supplement the communication capacity provided by traditional wired Local Area Networks (LANs) installed in the same geographic area as the WLAN system.

In short, wireless networks may exist to support wireless mobile communication devices (WMCDs). However, while WMCDs have continued to grow in complexity and capability, these WMCDs still continue to suffer from some major limitations, especially physical limitations and power.

Further limitations and disadvantages of conventional and traditional approaches will become apparent to one of skill in the art, through comparison of such systems with the present invention as set forth in the remainder of the present application with reference to the drawings.

BRIEF SUMMARY OF THE INVENTION

A method and/or system is provided for processing information based on detected biometric event data, substantially as shown in and/or described in accordance to at least one of the figures, as set forth more completely in the claims.

Various advantages, aspects and novel features of the present invention, as well as details of an illustrated embodiment thereof, will be more fully understood from the following description and drawings.

BRIEF DESCRIPTION OF SEVERAL VIEWS OF THE DRAWINGS

FIG. 1E illustrates an exemplary biometric event data mapping table based on data detected from biometric sensors, in accordance with an embodiment of the invention.

DETAILED DESCRIPTION OF THE INVENTION

Certain aspects of the invention may be found in a method and system for processing information based on detected biometric event data. Exemplary aspects of the invention may comprise capturing data and/or one or more events based on one or more detected biometric event data, and storing the captured data locally in a local host device and/or in a remote communication device. The captured data may be multimedia content data comprising text, speech, speech to text translation, video, still image, audio signal, or data received from analog or digital inputs. The captured data may be time, date or location stamped and concurrently tagged with detected biometric event data of one or more users in the vicinity. The captured data and the respective detected biometric event data may be mapped, analyzed, categorized and/or stored into respective databases in the memory for future retrieval.

Various data may be captured through a data acquisition system comprising one or more devices or sensors. The time, date and location information may be acquired through a GPS receiver and/or a combination of user data entry and/or from a network clock synchronization protocol. An information or data filtering system such as a user preference may be generated and/or used to retrieve and/or link captured data efficiently from the categorized stored captured data. The user preference may comprise a link to associated information such as the time, date, location stamps and the biometric event data, that may be utilized to identify the stored captured data. The biometric event data may be mapped to a biometric event data base such as a biometric event data mapping table unique to each user. Captured data may be retrieved by recalling or matching to one or more biometric event data experienced by one or more respective users from respective user preferences.

Figure 1A:
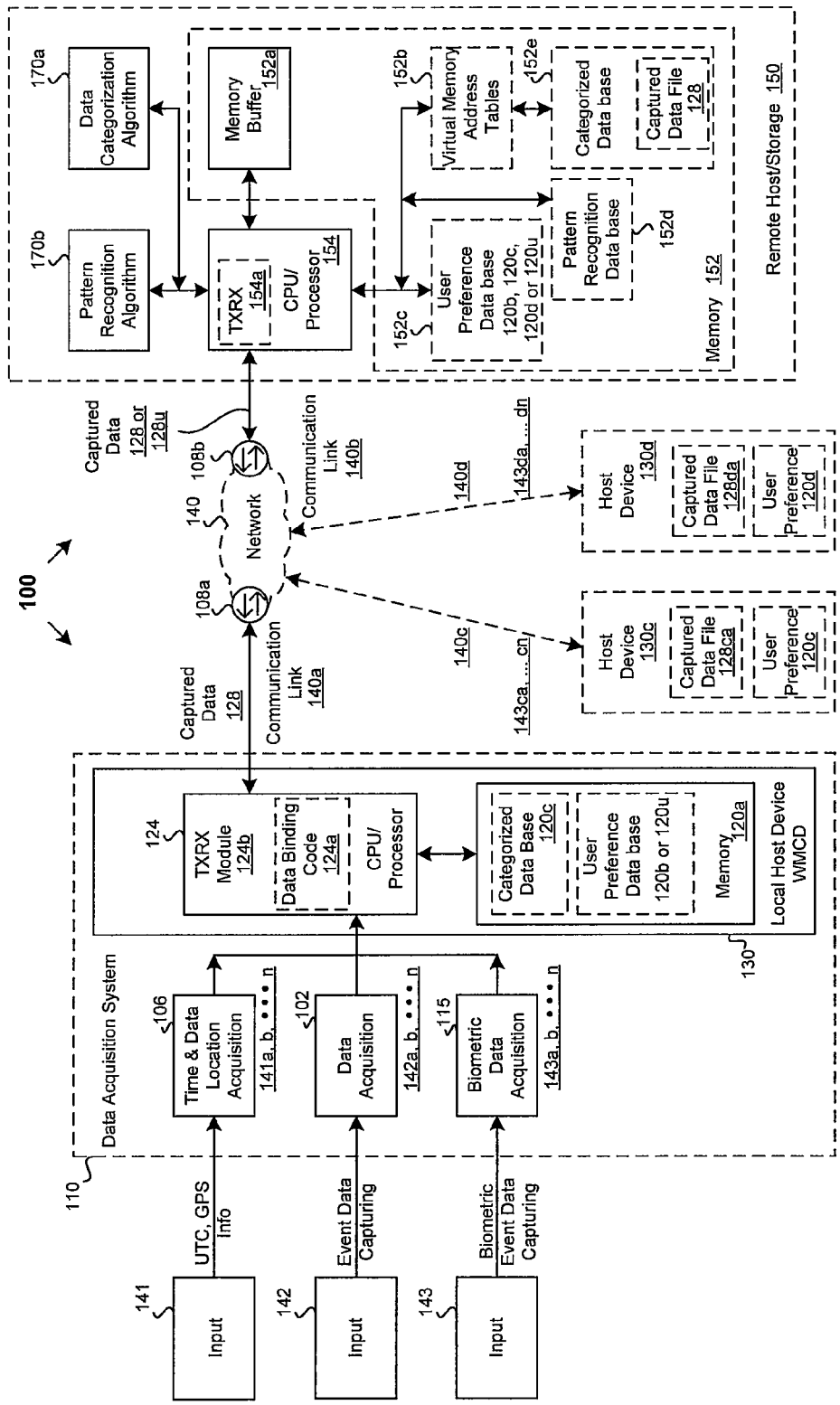
FIG. 1A is a block diagram of an exemplary data capturing system used for capturing data event based on user's biometric event data, in accordance with an embodiment of the invention.

FIG. 1A is a block diagram of an exemplary data capturing system used for capturing data event based on user's biometric event data, in accordance with an embodiment of the invention. Referring to FIG. 1A, there is shown an exemplary data capturing system 100 comprising a plurality of inputs 141, 142 and 143, a data acquisition system 110, an optional communication network 140 and an optional remote host or storage 150.

The input 141 may comprise at least one of the inputs of time, date and location information that may be obtained via GPS signals. The input 141 may be used for time, date and location stamping of data acquired from input 142. The input 141 of time information may be received in the format of local time, Coordinated Universal Time (UTC) or the Greenwich Mean Time GMT. A local time may be derived from the UTC based on the local geographical location. In another embodiment of the invention, the input 141 may utilize the IEEE 1588-2002 standard for a precision clock synchronized protocol to time stamp data communicated via a network such as the Ethernet. The location information of input 141 may be obtained via GPS signals, where location coordinates may be interpreted to provide detailed location such as street address, city name, zip code, or country code.

The input 142 may comprise event data or contents of interest intended for storage in the form of analog or digital signals. In an embodiment of the invention, the input 142 may comprise multimedia data content in the form of text, speech, speech to text translation, video, audio or still image data. Exemplary non-multimedia data content such as environmental data related to temperature, humidity, wind speed, air pressure, or ambient noise level may be included in the data content of input 142.

The input 143 may comprise biometric event data of a user that may be used to prompt or trigger data capturing of events from input 142. The biometric event data to input 143, may be classified into two main types: physiological and behavioral biometric event data. A physiological biometric event data may be data related to an event that tests, reads or captures a physical aspect of the body such as facial features, finger prints, hand shape, iris blood vessel pattern (iris scan), DNA sequences, pulse rate, pulse pressure, muscle tension. In addition to the biometric event data of an individual user, surrounding people in the vicinity may contribute biometric event data to the input 143 through additional host devices 130c and 130d where respective biometric event data from host devices 130c or 130d may be simultaneously communicated to the local host device 130 or to the remote host or storage 150 through communication links 140c and 140d.

A behavioral biometric event data may comprise data indicative of personality, or a behavior change in response to an event taking place. For example, handwriting, voice signature, a rise in pulse pressure, rise in pulse rate, skin temperature changes, sweating, pupil dilation, breathing rate change, change in tone of voice may indicate anxiety, anger, excitement, distress, rigorous physical activities, startle, fear, or mental unrest. Biometric event data from an Electroencephalogram (EEG) that detects brain wave may indicate mental state and mental activity. Speech pattern, tone of voice, speech to text translation and content analysis, galvanic skin response may provide biometric event data as an indication of the circumstances of the environment, type of stimulus received and a reaction to the stimulus.

The captured biometric event data may be utilized to construct or reconstruct a story or a journal of personal experience. A correlated set of time, date and location information along with biometric event data and data collected for an external event may be useful in devising a data linking path to speed up a search algorithm to identify captured events or stored data for future retrieval.

The data acquisition system 110 may comprise a plurality of data acquisition devices or sensors 102, 106, 115 and a local host device such as a wireless mobile communication device 130 (WMCD). In an embodiment of the invention, the plurality of data acquisition devices or sensors 102, 106, 115 may be discrete devices or sensors in a distributed system 110. The respective data from inputs 141, 142 and 143 may be communicated to the wireless mobile communication device WMCD 130 through wireless transmission such as using Bluetooth or Wireless Personal Area Network (WPAN) technology. For longer range transmission, a WLAN with a wireless access point, for example, may be used. In another embodiment of the invention, the plurality of data acquisition devices or sensors 102, 106, 115 may be integrated into fewer devices, or into a single wireless mobile communication device WMCD 130 forming an integrated data acquisition system 110. Alternately, a combination of distributed and integrated data acquisition system 110 may be used.

The data acquisition devices or sensors 102 may comprise a plurality of devices or sensors. For example a video camera may capture video content or motion pictures, a camera may capture still images, a scanner may capture text, graphics or still images, and a microphone. audio decoder or audio receiver may capture voice or audio data content. Non multimedia environmental sensors such as a thermocouple may capture temperature data, a hygrometer may capture humidity data, a pressure gauge may capture atmospheric pressure data, a Pitot tube may capture air flow velocity and a microphone may capture a ambient noise level. The captured data 142a, 142b to 142n from respective device or sensors 102 may be communicated to the WMCD 130 as digitized raw data, or may be communicated as formatted data frames.

The data acquisition device or sensor 106 may comprise a GPS receiver, a reference clock, time input from the IEEE 1588-2002 standard precision clock synchronized protocol or a data entry by a user at the start of recording the input 102. The data 141a, 141b to 141n may communicate time, date and location information to the WMCD 130 for synchronization with the captured data from respective data acquisition devices or sensors 102 and 115.

The data acquisition device or sensor 115 may comprise a plurality of biometric acquisition devices or sensors. For example, an EKG device with a plurality of electrodes may monitor heart activity, rate or pulse rate, an EEG device with a plurality of electrodes may monitor brain waves pattern and activities, a Galvanic skin response electrode or electrodermic sensor may monitor electrical resistance of the skin as indication of sympathetic activity and emotional arousal. Additionally, a scanner may scan finger print, facial feature, iris blood vessel pattern, monitor pupil dilation, eye movement. A thermal couple may monitor body temperature, a pressure transducer may monitor pulse pressure, a microphone, an audio receiver may record audio data, a voice encoder may encode voice and a conductance transducer may monitor body sweat. The acquired biometric event data 143a, 143b to 143n may be communicated to the WMCD 130 as digitized raw data, or may be communicated as a higher level interpreted data such as an emotional or mental state indication.

The wireless mobile communication device (WMCD) 130 may comprise a memory 120a, a CPU or a processor 124, and an integrated transmit/receive communication interface (TXRX module) 124b. The WMCD 130 may perform services and functions such as a smart mobile phone, a PDA and may communicate to external devices through wireless communications such as Bluetooth. The WMCD 130 may include other function as a local host device to perform a range of tasks such as data management, data binding or formatting the captured data 142a to 142n into another data format such as tagging captured data 128 for network transmission. In an embodiment of the invention, data binding codes 124a may be used to tag or pre-tag the captured data 142a to 142n with suitable identifications such as time, date or location data 141a to 141n and/or biometric event data 143a to 143n.

In an embodiment of the invention, the captured data 128 may be biometrically tagged and stored locally into the memory 120a in the WMCD 130. The captured data 128 may further be categorized and sorted based on the tagged information using for example, time, date, location, biometric event data and stored in a categorized data base 120c for future retrieval or processing. The pre-tagging or tagging of captured data 128 are discussed in U.S. patent application Ser. Nos. under 11/861,224 and 11/864,225 filed on even date herewith; and is hereby incorporated by reference in its entirety.

The WMCD 130 may store a user preference 120b for the captured data 128. The user preference 120b may comprise a link to associated information or data 141a to 141n such as the time, date, location stamps and the biometric event data 143a to 143n to identify the captured data 142a to 142n. The user preference 120b may be stored in the memory 120a of the WMCD 130, and may be triggered to retrieve captured data efficiently from the categorized data base 120c. The biometric event data 143a to 143n may be mapped to a biometric event data base unique to the respective person.

In another embodiment of the invention, additional multiple biometric event data 143ca to 143cn, 143da to 143dn from multiple users or host devices 130c or 130d may be concurrently or independently acquired when input data 142a to 142n are being captured by the local host device 130. The concurrently or independently acquired biometric event data 143ca to 143cn, 143da to 143dn may optionally be mapped, parsed, or appended to the captured data 128 from the local host device 130 and may optionally be stored as an updated captured data 128u locally in the host memory 120a or remotely in the memory 152 in the remote host or storage 150.

Optionally, one or more user preferences 120b, 120c or 120d may be specified to map or associate the biometric event data 143a to 143n, 143ca to 143cn, 143da to 143dn from the multiple users or host devices 130, 130c or 130d to link to the captured data 142a to 142n for later retrieval. Optionally, an updated user preference 120u may be specified to map or associate the biometric event data 143a to 143n, 143ca to 143cn, 143da to 143dn from the multiple users or host devices 130, 130c or 130d to link to the captured data 142a to 142n for later retrieval. By recalling or matching to one or more of biometric event data (i.e. 143a to 143n, 143ca to 143cn or 143da to 143dn) to one or more of the specified user preferences 120b, 120c or 120d or the updated multiple user preference 120u, the respective captured data 128 or the updated captured data 128u may be retrieved.

In another embodiment of the invention, the captured data 128 or 128u may be stored or further processed in an optional remote host or storage 150. For example, if the local host device 130 has limited memory for storage, it may be desirable to store the captured data 128 or 128u in the remote host or storage 150. Other reasons may be due to conserving the battery of the WMCD 130, limited processing capacity in the CPU/processor 124, or a lack of appropriate application to process the captured data 128 in the local host device 130.

The WMCD 130 may comprise suitable hardware, logic, circuitry, and/or code that may be adapted to provide wireless router functions to enable routing or transmission of respective data 141a to 141n, 142a to 142n, 143a to 143n as unprocessed raw data format to the remote host or storage 150 for further processing.

For remote processing, the transmit/receive TXRX module 124b may communicate the raw data 141a to 141n, 142a to 142n, 143a to 143n or the captured data 128 through a communication link 140a to the remote host or storage 150. The communication links 140a, 140b to the network 140 such as the Ethernet may be via a wired link or a wireless link. The communication links 140a, 140b may be encrypted for secured communication between the local host device of WMCD 130 and the remote host or storage 150.

The local host device WMCD 130 and the remote host or storage 150 may comprise suitable hardware, logic, circuitry, and/or code that may be adapted to provide wired or wireless networking operations through communication links 140a, 140b. The wired or wireless communication links 140a, 140b may be accessed from a WLAN infrastructure network 140 via a portal 108a and 108b. The portal 108a and 108b may comprise suitable hardware, logic, circuitry, and/or code and may be adapted to integrate the WLAN infrastructure network 140 with non-IEEE 802.11 networks. Moreover, the portal 108a and 108b may also be adapted to perform the functional operations of a bridge, such as range extension and/or translation between different frame formats, in order to integrate the WLAN infrastructure network 140 with IEEE 802.11-based networks.

In an embodiment of the invention, the remote host or storage 150 may comprise a CPU/processor 154, an integrated TXRX module 154a, a memory 152, one or more applications such as a data categorization algorithm and/or a pattern recognition algorithm. The remote host or storage 150 may have similar functions as the local host device WMCD 130, except may be with expanded capacity in the memory 152, the CPU/processor 154 processing power, or with the necessary operating system and applications for processing, categorizing, reading and writing the captured data 128 into the various data bases.

A data categorization algorithm 170a may be executed under an operating system by the CPU/Processor 154 in the memory buffer 152a to perform categorization on the captured data 128. The data categorization algorithm 170a may comprise one or more applications to sort and analyze one or more data segments according to the instructions provided in the header portion of the captured data 128. Further description of an exemplary data structure of the captured data 128 will be discussed with respect to FIG. 1D. In this exemplary data structure, the captured data 128 may comprise data segments to include user name, device type, time, date, location information, multimedia data and biometric event data. The data categorization algorithm 170a may generate or update a plurality of virtual memory address tables 152b that categorize and link respective data segments to physical memory locations in a categorized database 152e. The same data categorization algorithm 170a may be executed to perform categorical search in the virtual memory address tables 152b for data retrieval.

A pattern recognition algorithm 170b may be executed under an optional operating system by the CPU/Processor 154 in the memory buffer 152a to perform pattern recognition functions. The pattern recognition functions may comprise update or generation of pattern recognition data base 152d, user biometric event data check, authentication and verification. The pattern recognition algorithm 170b may comprise a plurality of biometric event data mapping applications and/or code, neural network intelligence application or artificial intelligence applications.

The pattern recognition algorithm 170b may analyze the collected biometric event data from the captured data 128 to infer mood, mental state, character portrayal, personality analysis, physical activities or health conditions at the input 141 time instances, when input event data 142 and 143 were captured. The pattern recognition analysis may comprise voice recognition, speech to text translation content analysis, speech pattern analysis, EEG brain waves pattern, eye movements, galvanic skin response, EKG pulse rate, breathing rate, pulse pressure, pupil dilation and muscle tension analysis.

The inferred results from the pattern recognition analysis may be dynamically generated or mapped to a category in a biometric event data mapping table 134 under the categorized database 152e. An unrecognized pattern may be generated and categorically stored as a new template with digitized biometric event data pattern in the pattern recognition data base 152d. A user preference 152c may be generated or dynamically updated to link the captured data 128 to the categorized data base 152e. The user preference 152c may comprise a plurality of instances with data tags that links the user preference 152c to the virtual memory address tables 152b such that data may be fetched from the categorized data base 152e based on linked address routes.

The information in the user preference 152c, the pattern recognition database 152d and the captured data 128aa in the categorized data base 152e from the remote host or storage 150 may be retrieved and communicated to the WMCD 130 or any available resources in a network upon user's request and upon successful authentication and verification of user's identity and user's preference 152c based on biometric event data. The generation of user's preferences and rendering of multimedia content on dissimilar format devices based on user's biometric event data is disclosed in U.S. application Ser. No. (11/861,219) titled "Method And System For Configuring Local And Remote Resources To Accomplish Rendering Of Multimedia Content On Dissimilar Format Devices Based On User Biometric Data" filed on even date herewith; and is incorporated herein by reference in its entirety.

Figure 1B:
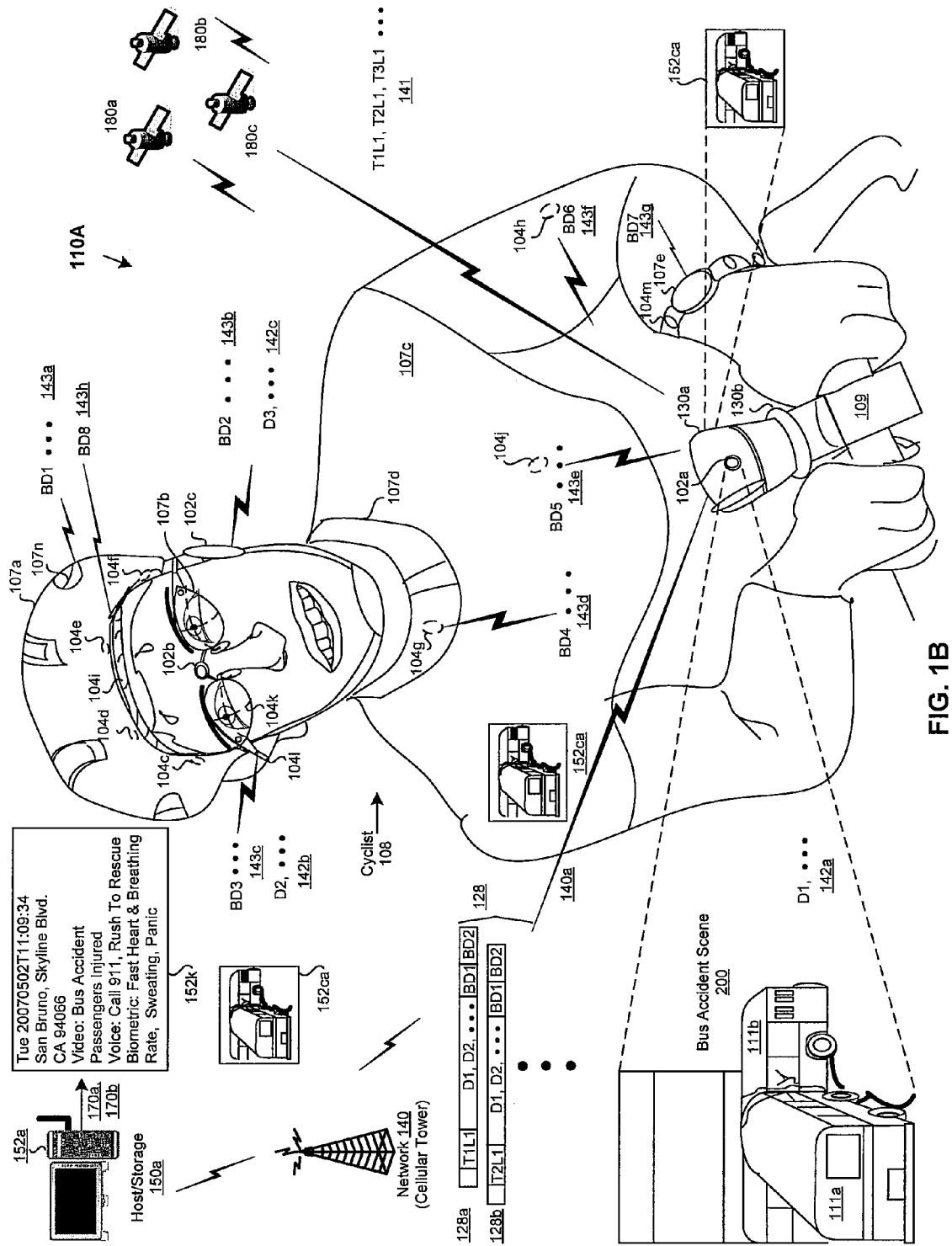
FIG. 1B illustrates an exemplary physical implementation of a data acquisition system capturing data content based on user's biometric event data, in accordance with an embodiment of the invention.

FIG. 1B illustrates an exemplary physical implementation of a data acquisition system capturing data content based on user's biometric event data, in accordance with an embodiment of the invention. Referring to FIG. 1B, there is shown a data acquisition system 110A worn by a user (Cyclist) 108 witnessing a bus accident scene or event 200 and triggering communication of a captured data 128 to a remote host or storage 150a through a wireless network 140a. The data acquisition system 110A may comprise a plurality of data acquisition devices and sensor such as a Bluetooth enabled hearing and speech device 102c, a Bluetooth enabled cyclist helmet 107a, a Bluetooth enabled cyclist goggle 107b, a Bluetooth enabled cyclist jersey 107c, a Bluetooth enabled wrist watch 107e, and a local host device such as a wireless mobile communication device (WMCD) 130a. Biometric event data comprises physiological biometric event data and behavioral biometric event data.

The Bluetooth enabled hearing and speech device 102c may capture and communicate the audio data D3 142c of the cyclist 108 such as an emergency 911 phone call via the WMCD 130b. The audio receiver of the Bluetooth enabled hearing and speech device 102c may pick up audio data D3 142c content including surrounding sound of the bus accident scene 200, the 911 operator dialogue content and the heavy breathing biometric event data BD2 143b of the cyclist 108 peddling towards the scene to render rescue to injured passengers. The audio data D3 142c and biometric event data BD2 143b may be communicated through Bluetooth wireless signals and stored into the WMCD 130a local memory. Alternately, the audio data D3 142c and biometric event data BD2 143b may be communicated to the remote host or storage 150a as captured data 128 through a communication link 140a such as a cellular network 140.

The Bluetooth enabled cyclist helmet 107a may capture and communicate the brain wave pattern of the cyclist 108 in response to witnessing the bus accident scene 200. The Bluetooth enabled cyclist helmet 107a may comprise a cyclist helmet with embedded EEG electrodes 104c, 104d, 104e and 104f to measure the left and right brain activities. The Bluetooth enabled cyclist helmet 107a may also comprise a thermocouple/conductance electrode 104i along the forehead of the cyclist 108 to measure the temperature and skin moisture conductivity data (sweat detection). The EEG brain wave data, temperature data and the moisture conductivity data may be communicated respectively as BD1 143a and BD8 143h through a patch antenna 107n on the Bluetooth enabled cyclist helmet 107a to the WMCD 130a through Bluetooth wireless signals.

The Bluetooth enabled cyclist goggle 107b may capture and communicate snap shots of still images of the scene, or detect eye movements and pupil dilation of the cyclist 108, in response to witnessing the bus accident scene 200 event. The Bluetooth enabled cyclist goggle 107b may comprise a camera 102b to capture still images of the bus accident scene 200 event as data D2 142b. In an embodiment of the invention, the goggle lens may be a scanner with targeting cross hair grids 104k to detect eye movement and pupil dilation, capturing biometric event data BD3 143c. The Bluetooth enabled cyclist goggle 107b may use a goggle frame antenna 104l to communicate data D2 142b and biometric event data BD3 143c to the WMCD 130a through Bluetooth wireless signals.

The Bluetooth enabled cyclist jersey 107c may capture and communicate biometric event data such as pulse rate, EKG heart rhythm, breathing pattern, muscle tension and Galvanic skin response of the cyclist 108, in response to witnessing the bus accident scene 200. The Bluetooth enabled cyclist jersey 107c may comprise embedded pressure transducers or electrodes 104g, 104h and 104j. Pressure transducers, or electrodes 104g may be embedded on the collar 107d to measure the pulse rate or Galvanic skin response as biometric event data BD4 143d. Pressure transducers or electrodes 104h may measure muscle tension or Galvanic skin response as biometric event data BD6 143f. Pressure transducers or electrodes 104j may measure the EKG heart rhythm or pulse rate or breathing pattern as biometric event data BD5 143e. The biometric event data BD4 143d to BD6 143f may be communicated to the WMCD 130a through Bluetooth wireless signals.

The Bluetooth enabled wrist watch 107e may capture and communicate biometric event data such as pulse rate, pulse pressure, EKG heart rhythm, muscle tension and Galvanic skin response of the cyclist 108, in response to witnessing the bus accident scene 200. In an embodiment of the invention, the Bluetooth enabled wrist watch 107e may function as a local host device with similar functions as the WMCD 130a such as a smart phone capable of communicating or transferring captured data 128 to the wireless network 140a. The Bluetooth enabled wrist watch 107e may comprise embedded pressure transducers or electrodes 104m capable of measuring pulse rate, pulse pressure, EKG heart rhythm, muscle tension and Galvanic skin response of the cyclist 108 as biometric event data BD7 143g. The biometric event data BD7 143g may be communicated to the WMCD 130a through Bluetooth wireless signals.

The WMCD 130a may capture and communicate video clips D1 142a or snap shots of still images of the bus accident scene 200 between buses 111a and 111b. In an embodiment of the invention, the video or still camera 102a on the WMCD 130a may follow the eye movements detected by the targeting cross hair grids 104k of the Bluetooth cyclist goggle 107b. The WMCD 130a may be mounted on a motorized micro gyro 130b on the bicycle frame 109 to allow radial movement mimicking the eye movement. In an embodiment of the invention, the WMCD 130a may comprise an optional GPS receiver to receive time, date, location data TL1 141 from a plurality of GPS satellites 180a to 180c.

In an embodiment of the invention, the WMCD 130a may perform data binding on the acquired multimedia data D1 142a, D2 142b, D3 142c and the biometric event data BD1 143a to BD8 143h, and transmit the captured data 128 as time, date and location stamped data frames 128a and 128b through wireless network 140a. In another embodiment of the invention, the WMCD 130a may not perform data binding. The captured multimedia data D1 142a, D2 142b, D3 142c and the biometric event data BD1 143a to BD8 143h may be time stamped by the IEEE 1588-2000 synchronized clock protocol and transmitted in the network 140.

In another embodiment of the invention, the WMCD 130a may generate a user preference 120b based on biometric event data at the time captured data 128 may be stored in the local memory or communicated to the remote host or storage 150a. The user preference 120b may link the biometric event data such as finger print, iris scan, voice recognition a behavioral condition or mental state of the cyclist 108 in the captured data 128. The user preference 120b may be used to gain future access to the network 140a or to search for captured data of the bus accident scene 200 through a process of user preference authentication, validation using a pattern recognition algorithm 170b.

The remote host or storage 150a may comprise similar functions as the remote host or storage 150 described in FIG. 1A. In an embodiment of the invention, the remote host or storage 150a may use the data categorization algorithm 170a and/or a pattern recognition algorithm 170b to analyze, construct a data mapping table, store a summary or synopsis 152k or generate a user preference icon 152ca with a bus accident scene. The icon 152ca may be communicated and stored locally in the user preference 120b in the form of a graphical user interface (GUI) such as the icon 152ca or as a compressed image file.

Figure 1C:
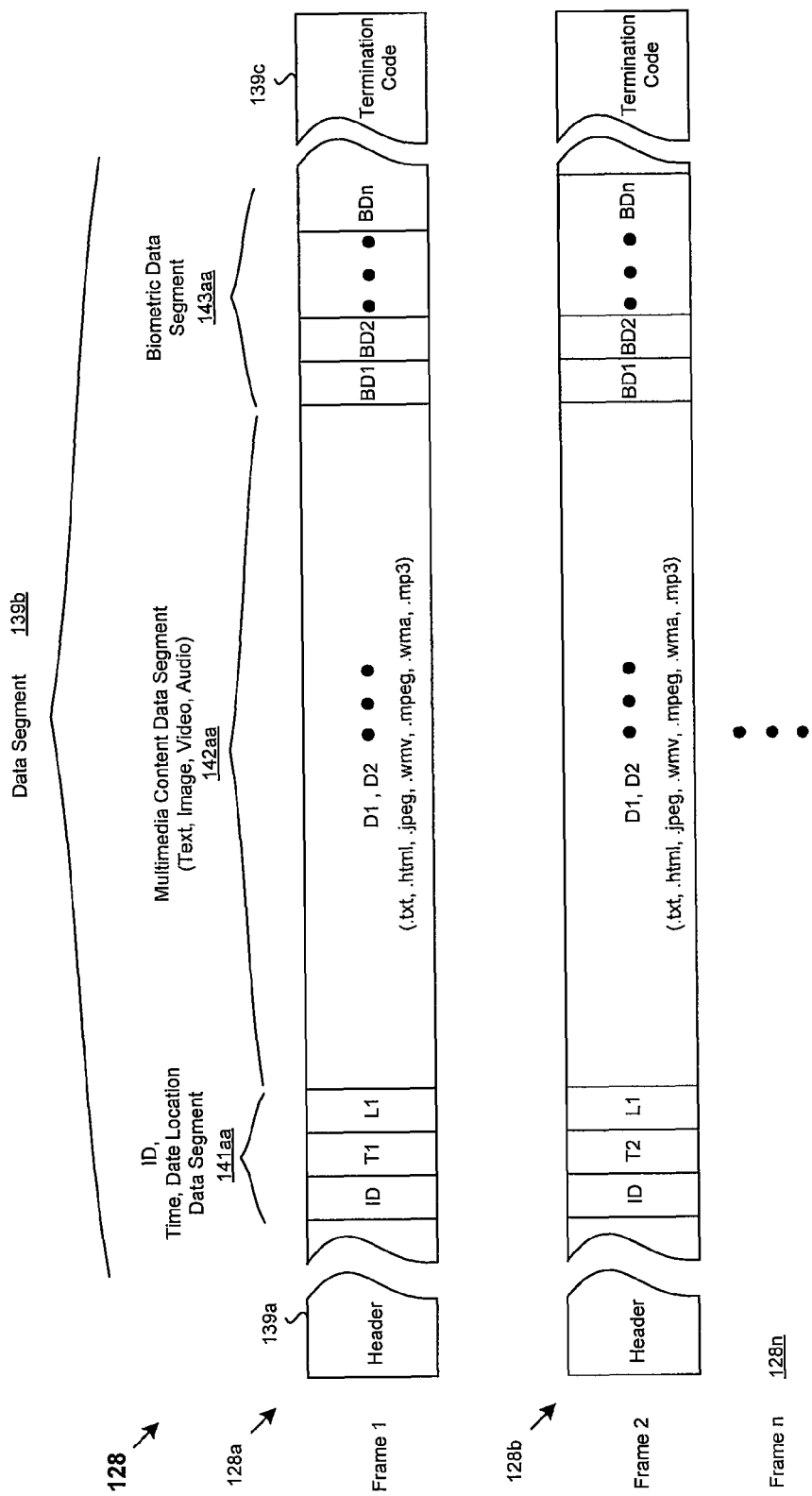
FIG. 1C illustrates exemplary data frame structure of captured data, in accordance with an embodiment of the invention.
Figure 1D:
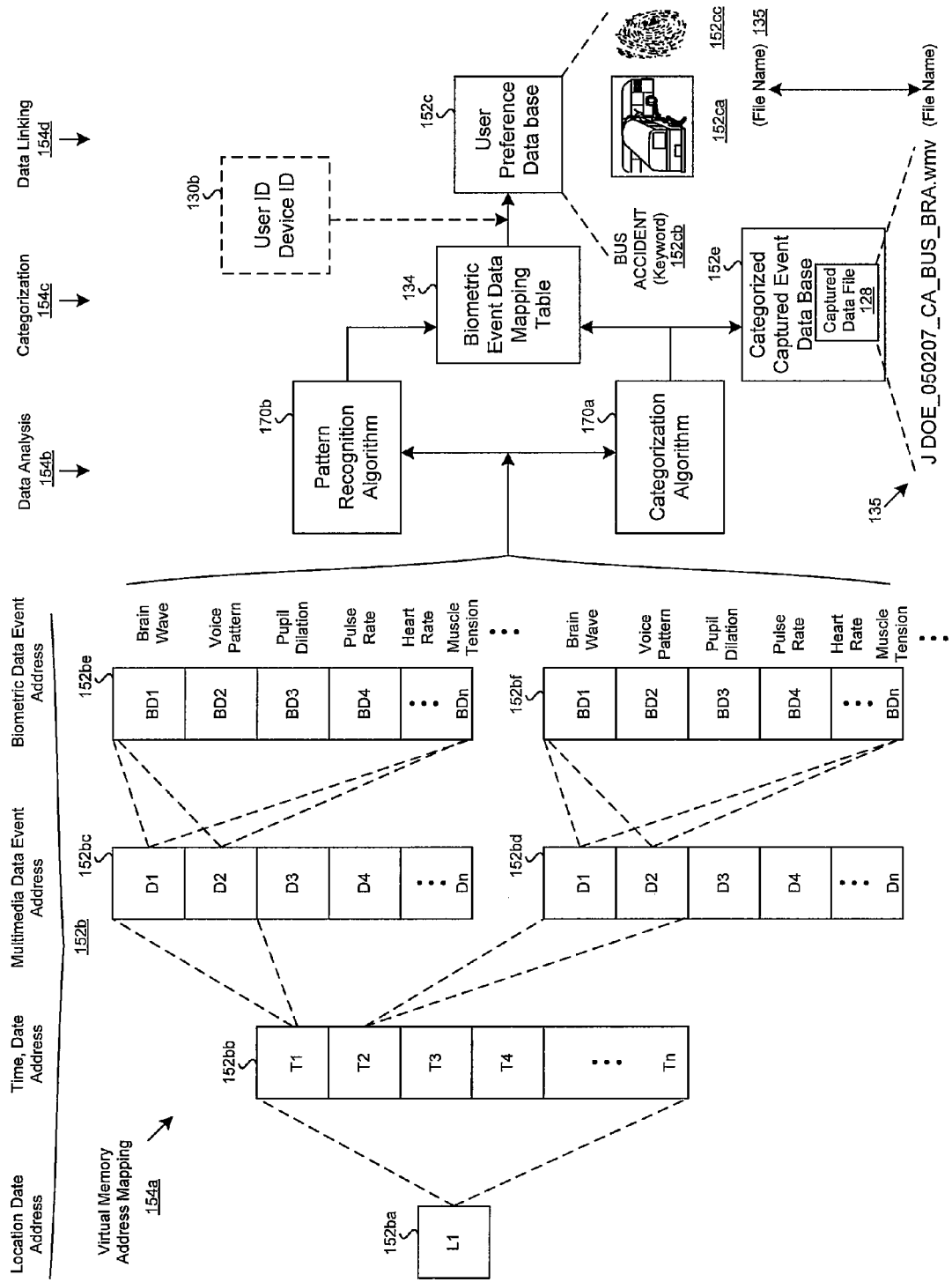
FIG. 1D illustrates an exemplary process of virtual memory address mapping and user preference generation based on biometric event data, in accordance with an embodiment of the invention.

In an alternate embodiment of the invention shown in FIG. 1D, the user preference may be a text keyword 152cb, a file name 135 or a biometric event data such as a finger print 152cc of the cyclist 108. In an alternate embodiment of the invention, the keyword may be a biometric event data such as a spoken phrase "BUS ACCIDENT" 152cb linking the captured data 128 or to the summary 152k of the bus accident scene or event 200 to be displayed on his WMCD 130a or other resources in the network.

To retrieve the data 128 from the memory 152, the cyclist 108 may select the icon 152ca from a GUI on his WMCD 130a, type in a "BUS ACCIDENT" keyword 152cb, speak the keyword phrase "BUS ACCIDENT" 152cb or use any biometric event data that may relate his experience of witnessing the bus accident scene 200 or describe a multimedia data from the bus accident scene 200 to trigger captured data 128 retrieval. The categorization algorithm 170a or pattern recognition algorithm 170b may search and retrieve the captured data 128 as a video clip, audio or text data from the local memory of the WMCD 130a or from the remote host or storage 150.

FIG. 1C illustrates an exemplary data structure of captured data frames, in accordance with an embodiment of the invention. Referring to FIG. 1C, there is shown an exemplary data structure of captured data 128 comprising a plurality of captured data frames 128a, 128b to 128n. In an embodiment of the invention, the WMCD 130a may comprise data binding codes 124a to bind respective captured data 141aa, 142aa and 143aa from the respective plurality of data acquisition devices or sensors 106, 102 and 115 into suitable communication format to form such as the exemplary captured data frames 128a.

The captured data frame 128a may comprise a header 139a, a data segment 139b and a termination code 139c. The header 139a may comprise data structure information and instructions to read and interpret the data segment 139b. The header information may comprise one or more headers to indicate data format, the start and stop bit of the data frame 128a, bit location of each data segment 141aa, 142aa and 143aa, type of data in each data segment, operating system, application program interfaces and network protocol information such as protocol standard, security permission level or network transport layer. The header instructions may comprise calling for one or more interpreter application to interpret and/or process the data segment 139b. In an event if more than one user's biometric data such as 143ca, 143da may be parsed into the data frame 128a, multiple headers may be used to specify the location or the start and stop bits of the respective biometric data 143ca or 143da in the biometric data segment 143aa.

The data segment 139b may comprise one or more types of data to be interpreted or processed. In this example, the data segment 139b may comprise three data segments 141aa, 142aa and 143aa. The data segment 141aa may comprise data relating to the identification of the data such as the name of the cyclist 108 (user), device ID, time, date or location information. Each data frame 128a may be time, date or optionally location stamped so that data may be categorized for storage or for retrieval in proper time sequence.

The data segment 142aa may comprise acquired multimedia content data, or external data directly transferred or imported to the WMCD 130a from other external devices. In an embodiment of the invention, the multimedia data may be text, still image, graphics, video, audio, speech or a combination of the data type. Data binding format may be in a suitable industry standard for transmission, display or for storage. For example, the multimedia data format may be designated by suffixes such as .txt (text keyboard) or .html (Hypertext Markup Language) for the text and web pages, .jpeg (Joint Photographic Experts Group) for the compressed still images or graphics, .wmv (Windows Media Video) or .mpeg (Motion Pictures Expert Group) for video or motion picture file, .wma (Windows Media Audio) or .mp3 (MPEG Layer 3) for audio or music file format.

The data segment 143aa may comprise acquired digitized readings from biometric devices or sensors. The digitized readings may be analog electrical signals or waveforms converted into digital format for transmission. In this example, the readings from the BD1 to BDn may represent readings of the EEG brain wave, Galvanic skin responses, speech pattern, voice pitch, Iris scanned image, finger print, pulse pressure, pulse rate, eye movements, pupil dilation response, conductivity, muscle tension, or EKG heart rhythm.

The termination code may comprise codes to terminate data frame reading, or parity check. A captured data 128 may comprise of sequences of time stamped captured data frames 128a to 128n. The content of the data segments 141aa, 142aa, 143aa may be extracted by one or more applications called out in the header 139a or in the CPU/processor 154 or 124 for processing.

FIG. 1D illustrates an exemplary process of virtual memory address mapping and user preference generation based on biometric event data, in accordance with an embodiment of the invention. Referring to FIG. 1D, there is shown a virtual memory address mapping step 154a, a data analysis step 154b (using applicable algorithms 170a and 170b), a data categorization step 154c (to generate a biometric event data mapping table 124 and categorized data base 152e) and a data linking step 154d (to generate user preference).

The virtual memory address mapping step 154a may comprise using a virtual memory address table 152b to map captured data 128 from a virtual memory address to a physical memory location. The virtual memory address table 152b may be an imaginary memory area supported by an operating system program such as an operating system in conjunction with the hardware associated with the memory 152. Since the captured data 128 may be striped over a distributed area on a memory device such as a RAID drive or on a flash memory, the virtual memory address table 152b may be a logical and convenient description for software programs to process captured data 128. Each of the data segments 141aa, 142aa and 143aa of data frames 128a to 128n is mapped into the new virtual memory location (or the respective physical memory locations) such as the biometric event data mapping table 124 and/or the categorized data base 152e.

The virtual memory address table 152b may be constructed from data extracted from each of data segments 141aa, 142aa and 143aa. In this example, the virtual memory address table 152b may comprise a location address column 152ba, a time and date address column 152bb, a multimedia data address column 152bc, 152bd and a biometric event data address column 152be and 152bf. The location address column 152ba may comprise of location data L1. In this example, the bus accident scene or event 200 may be recorded in the same vicinity or location L1. The time and date address column 152bb may comprise of time and date data T1 to Tn, corresponding to the respective data frames 128a to 128n.

The multimedia data address column 152bc, 152bd may comprise data D1 to Dn of the data segment 142aa corresponding to the first two captured data frames 128a and 128b. For example, the data D1 may be a video file, D2 may be an image file, D2 may be an audio file, D4 may be a text file. It is not necessary for the multimedia data address column 152bc or 152bd to have all of the mentioned data D1 to Dn be arranged in the ascending or descending order. The order may be random, so long as a linking path for each data D1 to Dn may be established with other related corresponding data.

The biometric event data address column 152be and 152bf may comprise biometric event data BD1 to BDn of the data segment 143aa corresponding to the first two captured data frames 128a and 128b. For example, the biometric event data BD1 may be from the EEG brain wave data of the left and/or right brain for brain activity analysis. The biometric event data BD2 may be from audio speech pattern, speech content, voice pitch for user recognition or for mood condition, mental state, and character or behavior analysis. The biometric event data BD3 may be eye movement detection, pupil dilation, iris scan.

The biometric event data BD4 may be for example pulse rate, pulse pressure, or Galvanic skin response data. The biometric event data BD5 to BDn may be from pulse rate, heart rate, EKG heart rhythm pattern, muscle tension, breathing rate. In certain instances, it may not be necessary for the biometric event data address column 152be or 152bf to have all of the mentioned biometric event data BD1 to BDn be arranged in the ascending or descending order. The order may be random, so long as a linking path for each biometric event data BD1 to BDn may be established with other related corresponding data.

In the data analysis step 154b and categorization step 154c, the time and date stamped multimedia data D1 to Dn and biometric event data BD1 to BDn may be analyzed separately or combined with other biometric event data using a categorization algorithm 170a and/or a pattern recognition algorithm 170b to generate a biometric event data mapping table 134. A categorized data base 152e may be generated from the multimedia data D1 to Dn. An exemplary captured data file name 135 "JDOE_050207_CA_BUS_BRA.wmv" in this example may be saved and named in the categorized data base 152e. The name of the data file 135 may be user defined, or may be generated from a default algorithm or from a related user preference based on the user ID, date or time stamp, location, a keyword of the event and/or designating a biometric event data such as a bravery act of the cyclist 108.

A user preference 152c may optionally be defined by a user cyclist 108, or may be generated by a user preference algorithm automatically in the WMCD 130a or remote host or storage 150. The user preference 152c such as a GUI object such as an icon or compressed image file 152ca of the bus accident, a spoken phrase or a text or keyword 152cb of "BUS ACCIDENT", or a biometric event data such as the finger print pattern 152cc of the cyclist 108 may be generated in the data linking step 154d. Based on the user preference 152c, the CPU/Processor 124 or 154 to execute one or more suitable programs using stored or captured data file 135 linked by a virtual memory addresses routes defined in the user preference 152c.

FIG. 1E illustrates an exemplary biometric event data mapping table based on data or readings detected from biometric sensors, in accordance with an embodiment of the invention. Referring to FIG. 1E, the exemplary biometric event data mapping table 134 may be generated from the results of data analysis step 154b and categorization step 154c described in FIG. 1D. In this example, the exemplary biometric event data mapping table 134 may suggest analyzed mapping results of biometric event data BD1 to BDn of captured data frames 128a to 128n. The suggested mapped results may have a physiological category comprising a physical condition column 134a and a behavioral category comprising a plurality of behavioral columns such as a mood condition column 134b, a mental state column 134c and a character condition column 134d.

Each of the categories, the physical condition 134a, the mood conditions 134b, the mental state 134c and the character conditions 134d may further be classified with a positive condition or a negative condition represented by P+, P−, E+, E−, M+, M− and C+, C− to describe the opposing conditions or to contrast the condition for comparison purpose. Other ways of categorizing the biometric event data mapping table 134 may be used. In another embodiment of the invention, a weighing factor or a range may be specified to describe the different degrees of physiological or behavioral conditions.

The biometric event data mapping table 134 may be populated with a plurality of commonly known health and psychological conditions or events to profile the cyclist's 108 reaction in witnessing the bus accident 200. In this example, to name a few, the cyclist's 108 physical condition 134a may be mapped with indications in column P+ of feeling physically strong from biometric event data BD1 (EEG brain waves), BD4 (Pulse rate), BD5 (EKG heart rhythm, heart rate), BD6 (muscle tension, Galvanic Skin Response), and BD7 (pulse rate). The cyclist's 108 voice was recorded as loud compared to normal condition from biometric event data BD2 (voice pattern, pitch, volume). The P− column may indicate the cyclist's 108 body was feeling hot from biometric event data BD4 (pulse rate) and BD8 (thermocouple reading, moisture reading from skin conductivity or Galvanic skin response) due to fast pedaling to the bus accident scene 200 to render rescue.

Likewise, the mood condition 134b may be mapped with indications in column E+ of feeling motivated from biometric event data BD1 (EEG brain waves), BD2 (speech content analysis, voice pattern), BD3 (eye movement, pupil dilation), BD6 (muscle tension, Galvanic Skin Response). The E− column may indicate the cyclist 108 was anxious from biometric event data BD1 (EEG brain waves), BD2 (speech content analysis, voice pattern), BD3 (eye movement, pupil dilation), BD4 (Pulse rate), BD5 (EKG heart rhythm, heart rate), BD6 (muscle tension, Galvanic Skin Response), BD7 (pulse rate) and BD8 (thermocouple reading, moisture reading from skin conductivity or Galvanic skin response).

Similarly, the mental state and character condition of the cyclist 108 may be found from the biometric event data mapping table 134 shown in FIG. 1E with respective highlighted mapped biometric event data. Each condition indicated in the biometric event data mapping table 134 may be generated from combining the results or inferences of data analysis 154b using the categorization algorithm 170a and the pattern recognition algorithm 170b described in FIG. 1D.

Figure 2:
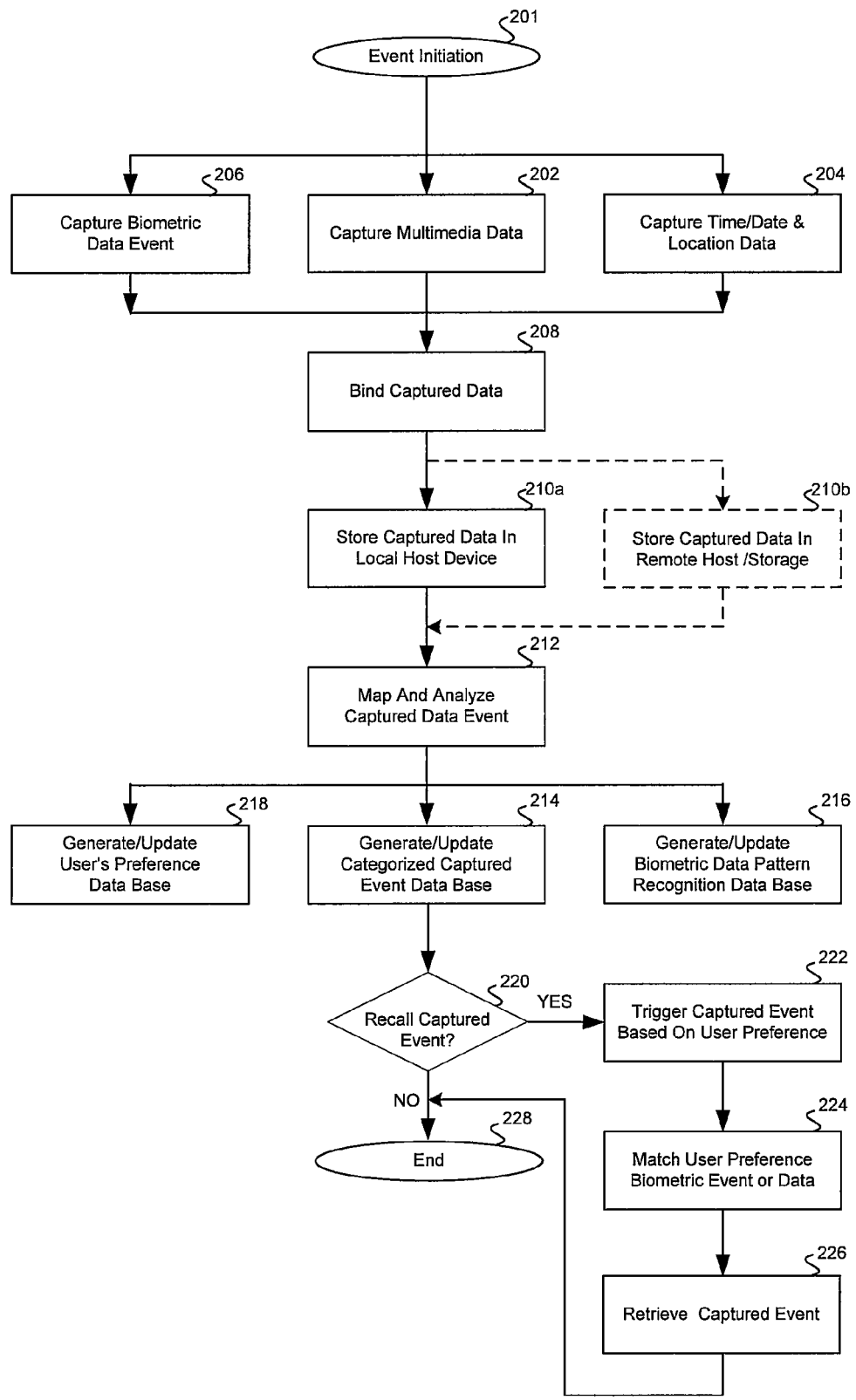
FIG. 2 is a flow diagram illustrating exemplary steps for capturing and storing of data based on detected biometric event data, in accordance with an embodiment of the invention.

FIG. 2 is a flow diagram illustrating exemplary steps for capturing and storing of data based on detected biometric event data, in accordance with an embodiment of the invention. Referring to FIG. 2 following start step 201, data acquisitions may take place in steps 202, 204 and 206. Step 202 may acquire or capture data input 142 from an event such as the bus accident scene or event 200. In step 202, the input data 142 may be captured as multimedia data 142a to 142n by a data acquisition system 102 comprising at least one or more devices or sensors such as a WMCD 130a (local host device), a Bluetooth enabled cyclist goggle 107b, and/or a Bluetooth enabled hearing and speech device 102c. The WMCD 130a may capture data text, video or still image multimedia data D1 142a, the Bluetooth cyclist goggle 107b may capture text, or still image multimedia data D2 142b, and the Bluetooth enabled hearing and speech device 102c may capture audio data D3 142c.

In step 204, time, date data T1 to Tn may be acquired via a reference clock, time data from the IEEE 1588-2002 standard precision clock synchronized protocol or a data entry by a user at the start of recording multimedia data 142a to 142n from data acquisition system 102. Optionally, location data L1 may be acquired with a GPS receiver. The time, date and/or location information may be used for time, date and/or location stamping of the acquired data 142a to 142n.

In step 206, a plurality of biometric devices or sensors such as the Bluetooth enabled hearing and speech device 102c, the Bluetooth enabled cyclist helmet 107a, the Bluetooth enabled cyclist goggle 107b, the Bluetooth enabled cyclist jersey 107c and the Bluetooth enabled wrist watch 107e may acquire biometric event data BD1 143a to BDn 143n such as biometric event data: EEG brain wave, Galvanic skin responses, speech pattern, voice pitch, Iris scanned image, finger print, pulse pressure, pulse rate, eye movement, pupil dilation, skin conductivity, muscle tension, or EKG heart rhythm.

In step 208, respective captured data 141a to 141n, 142a to 142n, 143a to 143n from respective data acquisition devices or sensors 106, 102, 115 in steps 202, 204 and 206 may be bound into suitable format for storage or for network communication. The captured multimedia data D1 142a to Dn 142n of the bus accident scene or event 200 may be respectively tagged and formatted into frames of captured data 128a to 128n with respective time, date and location stamping and biometric event data for local or remote storage. In another embodiment of the invention, the captured data from steps 202, 204 and 206 may be stored or communicated as raw data without the data binding step 208.

The captured data 128 may be stored locally in step 210a, or remotely in step 210b. In step 210a, the captured data 128 may be stored into the local memory 120a of the local host device such as the WMCD 130. Alternately, in step 210b, the captured data 128 may be communicated through the network 140 and stored remotely in a remote host or storage 150.

In step 212, captured data 128 from steps 210a or 210b may be virtually mapped to link data from physical memory 152 to a virtual memory address table 152b. The virtual memory address table 152b may comprise location addresses 152ba, time and date addresses 152bb, multimedia data addresses 152bc and 152bd, biometric event data addresses 152be and 152bf. The captured data 128 may be analyzed according to one or more corresponding data segments 141aa, 142aa, 143aa by one or more applications such as the categorization algorithm 170a and/or the pattern recognition algorithm 170b.

The analyzed data results of step 212 may be categorized to generate or update corresponding databases such as the categorized captured event data base 152e, the pattern recognition data base 152b and the user preference data base 152c. The categorized captured event data base 152e may be generated or updated in step 214 using the categorization algorithm 170a. The captured data 128 may be stored in the categorized data base 152e under a file name 135. The categorized captured data 128 may be sorted and searched according to time date, location, multimedia data content, or certain biometric event data.

The pattern recognition data base 152d may be generated or updated in step 216. A pattern recognition algorithm 170b may utilize captured biometric event data to generate a new pattern recognition data base 152d, or update an existing pattern recognition data base 152d. Analyzed biometric event data such as finger print, iris scan, pupil dilation, voice recognition, speech pattern, EEG brain wave pattern, EKG heart rhythm pattern, galvanic skin response, the physical condition 134a, the mood condition 134b, the mental state 134c or character condition 134d may be stored into the pattern recognition database 152d. In an embodiment of the invention, the pattern recognition database 152d may comprise a biometric event data mapping table 134.

The user preference data base 152c may be generated or updated in step 218. User preference for the captured bus accident scene or event 200 may be generated to trigger or recall the captured data 128. In an embodiment of the invention, the user preference may be an icon or compressed image 152ca, as a text, a keyword or a spoken phrase 152cb, or as a biometric event data characteristic to the cyclist 108 such as a finger print 152cc or a Galvanic skin response.

In step 220, there may be a request to recall the captured event 128. If the request may be confirmed, in step 222 user preference 152ca, 152cb or 152cc may be used to trigger for a search of the captured event or data 128. In step 224, the pattern recognition data base 152d may match one or more of the biometric event data such as data from the biometric event data mapping table 134 against the user preference 152ca, 152cb or 152cc. For example, the cyclist 108 may recall anxious feelings seeing a bus picture. The cyclist' 108 EEG brain wave pattern may be used by a pattern recognition algorithm 170b to match the biometric event data in the user preference data base 152c.

In instances when a match may be found with the user preference, the stored captured data event linked to the user preference may be retrieved from the WMCD 130 or from the remote host or storage 5 in step 226. In instances where there may be no request to recall captured data or event 128, or if the retrieval is completed, the process may terminate in step 228.

The steps of the process in FIG. 2 may be rearranged in a different order or substituted with similar or equivalent operation to accomplish the same results of capturing and storing of data based on detected biometric event data, without departing from the scope and spirit of the invention.

In accordance with various embodiments of the invention, the method for processing data 142a to 142n may comprise in a wireless communication device WMCD 130 capturing data such as time, date location data 141a to 141n, multimedia data 142a to 142n and biometric event data 143a to 143n based on a detected biometric event data. The time, date location data 141a to 141n may be captured by acquisition devices or sensors 106 such as a synchronized clock, a GPS receiver or network time input from IEEE 1588-2002 standard precision clock synchronized protocol.

The multimedia data 142a to 142n may be captured by data acquisition devices or sensors 102 such as the WMCD 130, the Bluetooth enabled hearing and speech device 102c, the Bluetooth enabled cyclist goggle 107b. The WMCD 130 may comprise a still camera or video camera 102a for still image or video data sensing. The Bluetooth enabled hearing and speech device 102c may comprise a microphone, a voice encoder, or an audio receiver for audio data capturing. The Bluetooth enabled cyclist goggle 107b may comprise a scanner or a camera 102b for still image data capturing.

The biometric event data 143a to 143n may be captured by data acquisition devices or sensors 115 such as the Bluetooth enabled hearing and speech device 102c, the Bluetooth enabled cyclist helmet 107a, the Bluetooth cyclist goggle 107b, the Bluetooth enabled cyclist jersey 107c and the Bluetooth enabled wrist watch 107e. Electrodes may be used to capture EEG brain wave pattern, a Bluetooth enabled hearing and speech device 102c to capture speech pattern, speech content, or voice recognition, electrodes or pressure transducer to capture pulse rate, pulse pressure, muscle tension, EKG heart rhythm or breathing rate, scanner to capture eye movement, pupil dilation or finger print or electrodes to capture Galvanic skin response.

The captured data 128 may be stored locally at the WMCD 130 or externally at a remote host or storage 150. The biometric event data such as pulse rate, pulse pressure, muscle tension, EKG heart rhythm, breathing rate, eye movement, pupil dilation, or finger print may comprise a physiological event. The biometric event data such as EEG brain wave pattern, speech pattern, speech content, voice recognition or Galvanic skin response may comprise a behavioral event.

The captured data 128 may comprise one or more of audio, video, still image and text content D1 142a, D2 142b, D3 142c, and capturing the captured data 128 may be based on user preference 152c. The user preference 152c may be modified or updated based on the captured data 128 and/or the biometric event data BD1 143a by linking the user preference 152c to the categorized data base 152e and/or to the biometric event data mapping table 134.

The captured data 128 may be retrieved locally from the WMCD 130 or externally from the remote host or storage 150 based on using the biometric event data from the user preference 152c to trigger the retrieval. A successful retrieval of the stored captured data 128 may be triggered by substantially matching from the pattern recognition database 152d a user's biometric event data such as the EEG brain wave pattern BD1 143a to the detected biometric event data stored in the user preference 152c using a pattern recognition algorithm 170b.

Certain embodiments of the invention may comprise a machine-readable storage having stored thereon, a computer program having at least one code section for processing information based on detected biometric event data, the at least one code section being executable by a machine for causing the machine to perform one or more of the steps described herein.

Accordingly, aspects of the invention may be realized in hardware, software, firmware or a combination thereof. The invention may be realized in a centralized fashion in at least one computer system or in a distributed fashion where different elements are spread across several interconnected computer systems. Any kind of computer system or other apparatus adapted for carrying out the methods described herein is suited. A typical combination of hardware, software and firmware may be a general-purpose computer system with a computer program that, when being loaded and executed, controls the computer system such that it carries out the methods described herein.

One embodiment of the present invention may be implemented as a board level product, as a single chip, application specific integrated circuit (ASIC), or with varying levels integrated on a single chip with other portions of the system as separate components. The degree of integration of the system will primarily be determined by speed and cost considerations. Because of the sophisticated nature of modern processors, it is possible to utilize a commercially available processor, which may be implemented external to an ASIC implementation of the present system. Alternatively, if the processor is available as an ASIC core or logic block, then the commercially available processor may be implemented as part of an ASIC device with various functions implemented as firmware.

The present invention may also be embedded in a computer program product, which comprises all the features enabling the implementation of the methods described herein, and which when loaded in a computer system is able to carry out these methods. Computer program in the present context may mean, for example, any expression, in any language, code or notation, of a set of instructions intended to cause a system having an information processing capability to perform a particular function either directly or after either or both of the following: a) conversion to another language, code or notation; b) reproduction in a different material form. However, other meanings of computer program within the understanding of those skilled in the art are also contemplated by the present invention.

While the invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiments disclosed, but that the present invention will include all embodiments falling within the scope of the appended claims.

What is claimed is:

1. A method for processing data, the method comprising:
in a wireless mobile communication device, performing by one or more processors, one or more circuits, or any combination thereof integrated within a single chip:
capturing data in the wireless mobile communication device;
concurrently capturing detected biometric event data via one or more biometric sensors independent of the knowledge of the captured data;
independently storing the captured data and the captured detected biometric event data; and
mapping at least a portion of the detected biometric event data to at least a portion of the captured data for later retrieval, wherein the mapping comprises mapping at least a portion of the detected biometric event data to a biometric event database, wherein the mapped at least portion of the detected biometric event data indicates a user's behavioral conditions during the capturing.

2. The method according to claim 1, comprising storing said captured data at said wireless communication device.

3. The method according to claim 1, comprising transferring said captured data for storage external to said wireless communication device.

4. The method according to claim 1, wherein said user's behavioral condition indicates one or more of user's mental state, character, and mood.

5. The method according to claim 1, wherein said mapping comprising analyzing said user's biometric event data to establish varying degrees of behavioral condition for contrast.

6. The method according to claim 1, wherein said captured data comprises one or more of audio, video, still image, and text content.

7. The method according to claim 1, comprising capturing said data based on a user preference.

8. The method according to claim 7, comprising modifying said user preference based on said captured data and/or said biometric event data.

9. The method according to claim 7, comprising matching said detected biometric event data with information in said user preference or a pattern recognition database for capturing.

10. The method according to claim 1, comprising detecting said biometric event data.

11. The method according to claim 1, comprising detecting said biometric event data via biometric sensor.

12. The method according to claim 1, wherein the biometric sensor comprises one or more of an EEG sensor, EKG sensor, a temperature sensor, a galvanic skin response sensor, audio sensor, and an optical scanner or sensor.

13. The method according to claim 1, wherein said wireless communication device comprises a capture device for said capturing of said data.

14. The method according to claim 13, wherein said capture device comprises one or more of a still camera, a video camera, a microphone, a text input device.

15. A system for processing data, the system comprising:
a wireless communication device comprising at least one processor, said at least one processor enables capturing of data;
at least one biometric sensor concurrently captures detected biometric event data independent of the knowledge of said captured data; and
a storage device stores said captured data and said captured detected biometric event data, and maps at least a portion of said stored captured data to at least a portion of said stored captured detected biometric event data for later retrieval, wherein said mapped at least said portion of said detected biometric event data indicates a user's behavioral conditions during said data capturing.

16. The system according to claim 15, wherein the wireless communication device comprises the storage device, and the at least one processor stores the captured data at the storage device of the wireless communication device.

17. The system according to claim 15, wherein said at least one processor transfers said captured data for storage external to said wireless communication device.

18. The system according to claim 15, wherein said user's behavioral condition indicates one or more of user's mental state, character, and mood.

19. The system according to claim 15, wherein said mapping comprises analyzing said user's biometric event data to establish varying degrees of behavioral condition for contrast.

20. The system according to claim 15, wherein said captured data comprises one or more of audio, video, still image, and text content.

21. The system according to claim 15, wherein said at least one processor captures said data based on a user preference.

22. The system according to claim 21, wherein said at least one processor modifies said user preference based on said captured data and/or said biometric event data.

23. The system according to claim 21, wherein said at least one processor matches said detected biometric event data with information in said user preference or a pattern recognition database for said capturing.

24. The system according to claim 15, wherein said at least one processor detects said biometric event data.

25. The system according to claim 15, wherein said at least on processor detects said biometric event data via biometric sensor.

26. The system according to claim 25, wherein said biometric sensor comprises one or more of an EEG sensor, EKG sensor, a temperature sensor, a galvanic skin response sensor, audio sensor, and an optical scanner or sensor.

27. The system according to claim 15, wherein said wireless communication device comprises a capture device for said capturing of said data.

28. The system according to claim 27, wherein said capture device comprises one or more of a still camera, a video camera, a microphone, a text input device.

* * * * *